United States Patent
Arai et al.

(10) Patent No.: US 9,181,160 B2
(45) Date of Patent: *Nov. 10, 2015

(54) METHOD OF PRODUCING 1-(2-T-BUTYLCYCLOHEXYLOXY)-2-BUTANOL

(71) Applicant: KAO CORPORATION, Chuo-ku (JP)

(72) Inventors: Tsubasa Arai, Wakayama (JP); Shinji Kotachi, Wakayama (JP); Yoshiharu Ataka, Wakayama (JP)

(73) Assignee: KAO CORPORATION, Chuo-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/368,381

(22) PCT Filed: Dec. 25, 2012

(86) PCT No.: PCT/JP2012/083455
§ 371 (c)(1),
(2) Date: Jun. 24, 2014

(87) PCT Pub. No.: WO2013/099858
PCT Pub. Date: Jul. 4, 2013

(65) Prior Publication Data
US 2014/0378713 A1    Dec. 25, 2014

(30) Foreign Application Priority Data

Dec. 26, 2011 (JP) .................................. 2011-284415
Dec. 26, 2011 (JP) .................................. 2011-284422

(51) Int. Cl.
| | |
|---|---|
| *C07C 41/00* | (2006.01) |
| *C07C 41/20* | (2006.01) |
| *C11B 9/00* | (2006.01) |
| *B01J 37/08* | (2006.01) |
| *B01J 21/18* | (2006.01) |
| *B01J 23/44* | (2006.01) |
| *B01J 23/46* | (2006.01) |
| *B01J 23/89* | (2006.01) |
| *B01J 37/02* | (2006.01) |

(52) U.S. Cl.
CPC .................. *C07C 41/20* (2013.01); *B01J 21/18* (2013.01); *B01J 23/44* (2013.01); *B01J 23/462* (2013.01); *B01J 23/464* (2013.01); *B01J 23/892* (2013.01); *B01J 37/0201* (2013.01); *B01J 37/084* (2013.01); *C11B 9/0034* (2013.01); *C07C 2101/14* (2013.01)

(58) Field of Classification Search
CPC .. C07C 2101/14; C07C 43/196; C07C 41/20; B01J 23/892; B01J 23/464; B01J 23/462; B01J 23/44; C11B 9/0034
USPC ............................................... 568/579
See application file for complete search history.

(56) References Cited

U.S. PATENT DOCUMENTS

| | | | |
|---|---|---|---|
| 5,194,423 A | 3/1993 | Koshino et al. | |
| 5,446,208 A | 8/1995 | Koshino et al. | |
| 2014/0350306 A1 | 11/2014 | Arai et al. | |

FOREIGN PATENT DOCUMENTS

| | | |
|---|---|---|
| EP | 2 799 417 A1 | 11/2014 |
| JP | 4-217937 | 8/1992 |
| JP | 4-327553 | 11/1992 |
| JP | 5-339188 | 12/1993 |
| JP | 6-263677 | 9/1994 |

OTHER PUBLICATIONS

International Search Report issued Mar. 19, 2013, in PCT/JP2012/083455, filed Dec. 25, 2012.
Christian Margot, et al., "Amber-Woody Scent: Alcohols with Divergent Structure Present Common Olfactory Characteristics and Sharp Enantiomer Differentiation", Helvetica Chimica Acta, vol. 87, No. 10, 2004, pp. 2662-2684.
U.S. Appl. No. 14/368,428, filed Jun. 24, 2014, Arai, et al.
Supplementary European Search Report dated Aug. 25, 2015 issued in corresponding European patent application No. 12 86 2276.

*Primary Examiner* — Jafar Parsa
(74) *Attorney, Agent, or Firm* — Oblon, McClelland, Maier & Neustadt, L.L.P.

(57) ABSTRACT

The present invention relates to [1] a method of producing 1-(2-t-butylcyclohexyloxy)-2-butanol including a step of hydrogenating 1-(2-t-butylphenyloxy)-2-butanol under a condition at a hydrogen pressure of from 1 to 5 MPa in the presence of a palladium catalyst (A) supported on peat-derived active carbon and a metal catalyst (B) containing one or more kinds of members selected from ruthenium, rhodium, platinum, and nickel; and [2] a perfume composition containing 1-(2-t-butylcyclohexyloxy)-2-butanol obtained by the foregoing method. According to the present invention, 1-(2-t-butylcyclohexyloxy)-2-butanol having a woody or amber-like fragrance as a perfume material and excellent fragrance notes can be obtained in a high purity because of a small remaining amount of a reaction intermediate and in a high yield.

20 Claims, No Drawings

METHOD OF PRODUCING 1-(2-T-BUTYLCYCLOHEXYLOXY)-2-BUTANOL

TECHNICAL FIELD

The present invention relates to a production method in which 1-(2-t-butylcyclohexyloxy)-2-butanol having excellent fragrance notes can be obtained in a high yield.

BACKGROUND ART

An α-(2-alkylcyclohexyloxy)-β-alkanol, especially 1-(2-t-butylcyclohexyloxy)-2-butanol, is a useful perfume material having a woody or amber-like fragrance and excellent persistence of aroma and capable of being inexpensively produced. For that reason, investigations regarding an efficient production method thereof are made.

For example, PTL 1 discloses (1) a method of converting a 2-alkylcyclohexanol by using a strong base into an alcoholate, which is then allowed to react with an epoxide; and (2) a method of allowing a 2-alkylphenol to react with an epoxide in the presence of a base catalyst, thereby forming an α-(2-alkylphenyloxy)-β-alkanol, which is then hydrogenated in the presence of a metal catalyst.

PTL2 discloses a production method by hydrogenating an α-(2-alkylphenyloxy)-β-alkanol in the presence of a catalyst containing (a) a palladium catalyst and (b) one or more kinds of members metal catalysts selected from ruthenium, rhodium, platinum, and nickel, for the purpose of obtaining an α-(2-alkylcyclohexyloxy)-β-alkanol having an excellent fragrance and a high trans-isomer content in a high yield within a short period of time.

In addition, PTL3 discloses a method of producing an ether alcohol by subjecting a cyclic ketal to hydrogenolysis in the presence of a catalyst containing 50% by weight or more of palladium and less than 50% by weight of one or more kinds of members selected from ruthenium, rhodium, platinum, and nickel.

CITATION LIST

Patent Literature

PTL 1: JP-A-4-217937
PTL 2: JP-A-4-327553
PTL 3: JP-A-6-263677

SUMMARY OF INVENTION

The present invention is concerned with the following [1] and [2].
[1] A method of producing 1-(2-t-butylcyclohexyloxy)-2-butanol including a step of hydrogenating 1-(2-t-butylphenyloxy)-2-butanol under a condition at a hydrogen pressure of from 1 to 5 MPa in the presence of a palladium catalyst (A) supported on peat-derived active carbon and a metal catalyst (B) containing one or more kinds of members selected from ruthenium, rhodium, platinum, and nickel.
[2] A perfume composition containing 1-(2-t-butylcyclohexyloxy)-2-butanol obtained by the method as set forth above in [1].

DESCRIPTION OF EMBODIMENTS

As described in PTLs 1 and 2, an α-(2-alkylcyclohexyloxy)-β-alkanol, especially 1-(2-t-butylcyclohexyloxy)-2-butanol, has an excellent woody or amber-like fragrance. However, according to the methods disclosed in PTLs 1 and 2, a reaction intermediate having a cyclic ketal in the cyclohexane ring remains in the obtained compound. Since this reaction intermediate is easily decomposed to produce a low-boiling offensive component, the fragrance of 1-(2-t-butylcyclohexyloxy)-2-butanol is adversely affected. Meanwhile, this reaction intermediate is difficult for removal by means of distillation or the like because its boiling point is close to that of the desired 1-(2-t-butylcyclohexyloxy)-2-butanol.

In addition, the present hydrogenation step involved such a problem that the yield is low because the formed 1-(2-t-butylcyclohexyloxy)-2-butanol causes hydrogenolysis to produces 1,2-butanediol or 2-t-butylcyclohexanol as a by-product.

For that reason, it is desirable to develop a production method of 1-(2-t-butylcyclohexyloxy)-2-butanol, in which the remaining of the reaction intermediate can be decreased, and the desired compound is obtained in a high yield.

The present invention relates to a production method in which 1-(2-t-butylcyclohexyloxy)-2-butanol having a woody or amber-like fragrance as a perfume material and excellent fragrance notes can be obtained in a high purity because of a small remaining amount of a reaction intermediate and in a high yield.

As for a production method in which 1-(2-t-butylcyclohexyloxy)-2-butanol having a small remaining amount of a reaction intermediate and a high purity can be obtained in a high yield, the present inventors have found that the above-described problem can be solved by carrying out hydrogenation at a low hydrogen pressure in the presence of a palladium catalyst supported on peat-derived active carbon and a specified metal catalyst.

Specifically, the present invention is concerned with the following [1] and [2].
[1] A method of producing 1-(2-t-butylcyclohexyloxy)-2-butanol including a step of hydrogenating 1-(2-t-butylphenyloxy)-2-butanol under a condition at a hydrogen pressure of from 1 to 5 MPa in the presence of a palladium catalyst (A) supported on peat-derived active carbon and a metal catalyst (B) containing one or more kinds of members selected from ruthenium, rhodium, platinum, and nickel.
[2] A perfume composition containing 1-(2-t-butylcyclohexyloxy)-2-butanol obtained by the method as set forth above in [1].

According to the present invention, a production method in which 1-(2-t-butylcyclohexyloxy)-2-butanol having a woody or amber-like fragrance as a perfume material and excellent fragrance notes can be obtained in a high purity because of a small remaining amount of a reaction intermediate and in a high yield can be provided.

Production method of 1-(2-t-butylcyclohexyloxy)-2-butanol

The production method of 1-(2-t-butylcyclohexyloxy)-2-butanol according to the present invention includes a step of hydrogenating 1-(2-t-butylphenyloxy)-2-butanol under a condition at a hydrogen pressure of from 1 to 5 MPa in the presence of a palladium catalyst (A) supported on peat-derived active carbon and a metal catalyst (B) containing one or more kinds of members selected from ruthenium, rhodium, platinum, and nickel.
<Palladium Catalyst (A)>

In the present invention, the palladium catalyst (A) supported on peat-derived active carbon is used in the hydrogenation step.

In the present invention, the palladium catalyst (A) refers to the whole of palladium and the peat-derived active carbon that is a carrier.

Examples of the active carbon include, in addition to peat-derived active carbon, active carbons derived from bituminous coal, anthracite coal, lignite, wood, coconut shell, or the like. The peat-derived active carbon which is used in the present invention is especially preferable from the viewpoint of revealing the activity of the palladium catalyst.

In the present invention, since the hydrogenation step is carried out by using the palladium catalyst (A) supported on this peat-derived active carbon at a low hydrogen pressure as from 1 to 5 MPa, 1-(2-t-butylcyclohexyloxy)-2-butanol having a woody or amber-like fragrance and excellent fragrance notes can be obtained in a high purity because of a small remaining amount of a reaction intermediate and in a high yield. While the reason for this is not elucidated yet, the following may be considered.

As the reaction intermediate in the present hydrogenation reaction, the above-described cyclic ketal and enol ether alcohol may be considered, and it may be considered that an equilibrium reaction is occurred due to rearrangement. In such reaction intermediates, it may be considered that enol ether alcohol has high reactivity to the hydrogenation, so that the desired compound is obtained by that hydrogenation. For that reason, it may be considered that in the present hydrogenation reaction, the hydrogenation reaction of enol ether alcohol proceeds more preferentially than the occurrence of a rearrangement reaction of enol ether alcohol from the cyclic ketal, so that the cyclic ketal remains.

In the present invention, it may be considered that by carrying out the reaction by using peat-derived active carbon having a low carbon content and containing a lot of components such as sulfur, a heavy metal, etc. as the carrier of the palladium catalyst under a low hydrogen pressure condition, the hydrogen adsorption amount onto the catalyst is decreased, the hydrogenation reaction is suppressed, and a catalytic active site onto which hydrogen does not adsorb catalyzes the rearrangement reaction from the cyclic ketal into enol ether alcohol, thereby allowing the reaction to proceed; and therefore, the remaining amount of the cyclic ketal that is a reaction intermediate becomes small, and the obtained 1-(2-t-butylcyclohexyloxy)-2-butanol has a high purity, so that it has a woody or amber-like fragrance and excellent fragrance notes.

In addition, it may be considered that the reaction is carried out under a low hydrogen pressure condition, and hence, the hydrogenolysis of 1-(2-t-butylcyclohexyloxy)-2-butanol is hardly caused, 1,2-butanediol or 2-t-butylcyclohexanol is not produced as a by-product, and the desired 1-(2-t-butylcyclohexyloxy)-2-butanol can be obtained in a high yield.

(Production of Peat-Derived Active Carbon)

The peat-derived active carbon can be, for example, obtained by carbonizing a peat-derived carbon material produced in the usual way, activating it by a known method, and then dipping the resultant in a dilute hydrochloric acid to remove an alkali component contained in the active carbon, followed by washing with water and drying.

Examples of the activation method of the active carbon include a gas activation method by activating the active carbon with an oxidizing gas (e.g., water vapor, carbon dioxide, air, combustion gas, or the like) at from 700 to 900° C.; and a chemical activation method by adding or penetrating the active carbon with a chemical such as zinc chloride, calcium chloride, magnesium chloride, phosphoric acid, etc. and then shutting off the air to achieve activation at from 500 to 700° C.

Of these, from the viewpoint of revealing the activity of the palladium catalyst, the peat-derived active carbon activated by the gas activation method is preferable.

From the viewpoint of catalytic activity, the carbon content in the peat-derived active carbon is preferably from 95 to 99.95% by mass, and more preferably from 97 to 99.9% by mass.

(Form of Active Carbon)

The shape of the active carbon is not particularly limited, and it may be a shape of powder, granule, fiber, pellet, honeycomb, or the like.

From the viewpoint of enhancing the catalytic activity, an average pore diameter of the active carbon is preferably from 8 to 100 angstroms, more preferably from 8 to 60 angstroms, and still more preferably from 30 to 60 angstroms.

A pore volume of the active carbon (pore volume of pores having a pore diameter of less than 1,000 angstroms) is preferably from 0.1 to 2.5 mL/g, and from the viewpoint of catalytic activity, the pore volume of the active carbon is more preferably from 0.1 to 2.0 mL/g, still more preferably from 0.2 to 1.5 mL/g, yet still more preferably from 0.2 to 1.0 mL/g, and even yet still more preferably from 0.3 to 1.0 mL/g.

In addition, from the viewpoint of catalytic activity and the viewpoint of enhancing the yield, a pore volume of meso pores of the peat-derived active carbon (pore volume of pores having a pore diameter of from 2 to 50 nm) which is used in the present invention is preferably 0.21 mL/g or more, more preferably 0.24 mL/g or more, still more preferably 0.27 mL/g or more, and yet still more preferably 0.30 mL/g or more, and preferably not more than 1.0 mL/g, more preferably not more than 0.75 mL/g, and still more preferably not more than 0.4 mL/g.

From the viewpoint of enhancing the catalytic activity, a specific surface area of the active carbon is preferably from 100 to 3,000 $m^2/g$, more preferably from 100 to 2,000 $m^2/g$, and still more preferably from 150 to 1,500 $m^2/g$.

The above-described average pore diameter, pore volume, pore volume of meso pores, and specific surface area of the active carbon are measured by the mercury intrusion method using a dry catalyst powder.

(Preparation of Palladium Catalyst (A) Supported on Peat-Derived Active Carbon)

Examples of a method of supporting palladium on peat-derived active carbon include an impregnation method, an ion exchange method, a CVD method, and the like, an impregnation method and an ion exchange method are preferable, and an impregnation method is more preferable.

In order to support palladium on peat-derived active carbon, it is preferable to use a palladium salt.

Examples of the palladium salt which is used for the purpose of supporting palladium thereon include one or more kinds of members selected from $Pd(OH)_2$, $PdCl_2$, $Pd(OAc)_2$, $Pd(NH_4)Cl_2$, and $[Pd(NH_3)_4]Cl_2$. Of these, one or more kinds of members selected from palladium hydroxide: $Pd(OH)_2$, palladium chloride: $PdCl_2$, and palladium acetate: $Pd(OAc)_2$ are preferable, and one or more kinds of members selected from palladium hydroxide and palladium chloride are more preferable. Examples of the impregnation method using a palladium salt include a method of dissolving a palladium salt in an appropriate solvent and dispersing and contacting the peat-derived active carbon, or the like.

The supporting amount of palladium on the peat-derived active carbon is preferably from 0.1 to 15% by mass, more preferably from 0.5 to 10% by mass, and still more preferably from 1 to 5% by mass in the palladium catalyst (A). When the supporting amount of palladium is less than 0.1% by mass, the catalytic activity becomes easily insufficient, whereas when it is more than 15% by mass, the possibility of giving an adverse influence such as sintering, etc. becomes high on the occasion of supporting.

After supporting palladium on the peat-derived active carbon, for example, the resultant is allowed to stand under a hydrogen gas stream, or added with a reducing agent such as formaldehyde, hydrazine, sodium borohydride, etc., and subjected to a reducing treatment at a temperature of from about 20 to 300° C., and preferably from 80 to 280° C., upon heating as the need arises; thereafter, solid-liquid separation is carried out; and the obtained solid is washed with water and dried, whereby the palladium catalyst (A) supported on peat-derived active carbon can be obtained.

The pH of the palladium catalyst (A) is preferably from 7.0 to 12.0, and from the viewpoints of enhancing the yield and rendering the fragrance notes of the obtained 1-(2-t-butylcyclohexyloxy)-2-alkanol favorable, the pH of the palladium catalyst (A) is preferably from 7.0 to 10.0, more preferably from 7.0 to 9.0, still more preferably from 7.5 to 9.0, yet still more preferably from 7.8 to 8.9, and even yet still more preferably from 7.9 to 8.8.

Incidentally, the pH of the palladium catalyst (A) refers to a pH of a mixture obtained by mixing the palladium catalyst (A) with pure water in an amount of 10 times by mass.

In addition, from the viewpoints of accelerating an isomerization reaction to decrease the reaction intermediate and accelerating the isomerization to enhance the trans-isomer content, it is preferable that the palladium catalyst (A) contains a metal, nitrogen, and sulfur.

Examples of the metal include one or more kinds of members selected from iron, magnesium, manganese, calcium, and titanium. A total content of the metal is preferably 0.10% or more, more preferably 0.15% or more, still more preferably 0.20% or more, and yet still more preferably 0.24% or more, and preferably not more than 1.0%, more preferably not more than 0.80%, still more preferably not more than 0.50%, and yet still more preferably not more than 0.40% in the palladium catalyst (A).

The above-described content of the metal is one measured by carrying out the high-frequency inductively coupled plasma (ICP) emission spectrometry with respect to iron, magnesium, manganese, calcium, and titanium on a sample obtained by subjecting a dry catalyst powder to wet decomposition with sulfuric acid, nitric acid, and hydrogen peroxide.

The content of nitrogen is preferably 0.07% or more, more preferably 0.08% or more, still more preferably 0.09% or more, and yet still more preferably 0.10% or more, and preferably not more than 1.0%, more preferably not more than 0.50%, still more preferably not more than 0.20%, and yet still more preferably not more than 0.15% in the palladium catalyst (A).

The content of nitrogen is measured by the chemiluminescence method using a dry catalyst powder.

The content of sulfur is preferably 0.08% or more, more preferably 0.09% or more, still more preferably 0.10% or more, and yet still more preferably 0.11% or more, and preferably not more than 1.0%, more preferably not more than 0.50%, still more preferably not more than 0.20%, and yet still more preferably not more than 0.15% in the palladium catalyst (A).

The content of sulfur is measured by the combustion ion chromatography using a dry catalyst powder.

<Metal Catalyst (B)>

In the present invention, the metal catalyst (B) containing one or more kinds of members selected from ruthenium, rhodium, platinum, and nickel is used in addition to the above-described palladium catalyst (A).

Among the above-described metal components which are used for the metal catalyst (B), from the viewpoint of enhancing the yield and the trans-isomer content and the viewpoint of decreasing the remaining amount of the reaction intermediate, ruthenium, rhodium, and platinum are preferable, ruthenium and rhodium are more preferable, and ruthenium is still more preferable.

The metal catalyst (B) is preferably a supported catalyst supported on a carrier. The carrier is preferably an inorganic carrier. Examples of the inorganic carrier include one or more kinds of carriers selected from active carbon, alumina, silica, silica magnesia, and zeolite. Of these, active carbon is more preferable from the viewpoint of catalytic activity.

From the viewpoint of preventing sintering while increasing the catalytic activity, the supporting amount of the metal component is preferably from 0.05 to 20% by weight, more preferably from 0.1 to 15% by weight, and still more preferably from 0.5 to 10% by weight of the whole of the metal catalyst (B).

In the case where the metal catalyst (B) is a supported catalyst, the metal catalyst (B) refers to the whole including the metal and the carrier.

(Preparation of Metal Catalyst (B))

The preparation of the metal catalyst (B) can be carried out by a known method. For example, when the case of using ruthenium as the metal component is taken as an example, first of all, the above-described inorganic carrier is added to and suspended in a medium such as ion-exchanged water, etc.; a solution having a ruthenium compound (e.g., a chloride, nitrate, formate, or ammonium salt of ruthenium, or the like) dissolved in an aqueous solvent such as ion-exchanged water, etc. is added to this suspension; and the resultant adjusted to a temperature of from about 20 to 95° C. while stirring, upon heating as the need arises. Subsequently, an alkali (e.g., ammonia water, a carbonate or hydroxide of an alkali metal such as sodium, potassium, etc., or the like) is added to the resulting suspension to adjust the pH to from about 4 to 12, thereby achieving hydrolysis, followed by ageing to support the ruthenium component on the inorganic carrier.

Subsequently, for example, a reducing agent such as formaldehyde, hydrazine, sodium borohydride, etc. is added; the resultant is subjected to a reducing treatment under a hydrogen gas stream at a temperature of from about 20 to 95° C., upon heating as the need arises; thereafter, solid-liquid separation is carried out; and the obtained solid is washed with water and dried, whereby the metal catalyst (B) can be obtained.

From the viewpoint of enhancing the yield of 1-(2-t-butylcyclohexyloxy)-2-butanol, the pH of the metal catalyst (B) is preferably from 6.0 to 12.0, more preferably from 7.0 to 9.0, and still more preferably from 7.2 to 8.0. Incidentally, the pH of the metal catalyst (B) refers to a pH of a mixture obtained by mixing the metal catalyst (B) with pure water in an amount of 10 times by mass.

(Palladium Catalyst (A) and Metal Catalyst (B))

From the viewpoint of catalytic activity, a mass ratio of the palladium catalyst (A) and the metal catalyst (B), [(A)/(B)], is preferably from 1,000/1 to 1/1, and more preferably from 100/1 to 5/1.

In addition, from the viewpoint of enhancing the yield and the trans-isomer content, a mass ratio of palladium in the palladium catalyst (A) and the metal in the metal catalyst (B), [{palladium in the catalyst (A)}/{metal in the catalyst (B)}], is preferably from 80/20 to 99/1, more preferably from 85/15 to 95/5, and still more preferably from 90/10 to 95/5.

A mixing method of the palladium catalyst (A) and the metal catalyst (B) is not particularly limited. Examples thereof include (i) a method of separately adding the catalysts (A) and (B) at the time of the reaction; (ii) a method of preparing a mixed catalyst such as a coprecipitation catalyst, etc. prior to the reaction; and the like. From the viewpoint of adjusting the mass ratio of the palladium catalyst (A) and the metal catalyst (B), the method (i) of separately adding the catalysts (A) and (B) at the time of the reaction is preferable.

From the viewpoints of enhancing the yield and decreasing the reaction intermediate, a total use amount of the palladium catalyst (A) and the metal catalyst (B) is preferably from 0.01 to 10% by mass, and more preferably from 0.05 to 5% by mass relative to 1-(2-t-butylphenyloxy)-2-butanol as the raw material.

<Hydrogenation Step>

In the hydrogenation step in the present invention, the hydrogenation reaction is, for example, carried out by mixing 1-(2-t-butylphenyloxy)-2-butanol, the palladium catalyst (A), and the metal catalyst (B) containing one or more kinds of members selected from ruthenium, rhodium, platinum, and nickel, preferably in a use amount falling within the above-described range in a pressure-resistant reactor such as an autoclave, etc., and adding an arbitrary organic solvent as the need arises, and further introducing hydrogen into the reactor such that the hydrogen pressure is from 1 to 5 MPa.

Examples of the organic solvent which is used for the hydrogenation reaction include one or more kinds of members selected from an alcohol and a hydrocarbon. Examples of the alcohol include methanol, ethanol, isopropanol, and the like, and examples of the hydrocarbon include hexane, cyclohexane, and the like. Of these, an alcohol is preferable, and isopropanol is more preferable.

From the viewpoint of productivity, the amount of the organic solvent is preferably not more than 50% by mass relative to 1-(2-t-butylphenyloxy)-2-butanol. From the viewpoint of obtaining 1-(2-butylcylohxexyloxy)-2-butanol having a high trans-isomer content, a strong woody or amber-like fragrance, and excellent fragrance notes in a high yield, the amount of the organic solvent is more preferably not more than 10% by mass, still more preferably not more than 5% by mass, yet still more preferably not more than 1% by mass, even still more preferably substantially 0% by mass, and even yet still more preferably 0% by mass. It is even still more preferable that the organic solvent is not contained. That is, when the hydrogenation reaction is carried out in the absence of a solvent, while the hydrogenation reaction gently proceeds, the contact between the substrate and the catalyst is accelerated; the isomerization reaction of an intermediate rapidly proceeds; the remaining amount of the reaction intermediate is decreased; and a lot of thermodynamically stable trans-isomers are obtained, and hence, such is preferable.

In the hydrogenation step of the present invention, by making the hydrogen pressure relatively low as from 1 to 5 MPa, the hydrogenation reaction gently proceeds. In particular, in the case of using the palladium catalyst (A) supported on peat-derived active carbon, as described above, it may be considered that the rearrangement reaction from the reaction intermediate cyclic ketal to enol ether alcohol efficiently proceeds. From the viewpoint of obtaining 1-(2-t-butylcyclohexyloxy)-2-butanol having a small remaining amount of the reaction intermediate and a high purity in a high yield, the above-described hydrogen pressure is preferably from 1 to 4 MPa, more preferably from 1.5 to 4.0 MPa, still more preferably from 2.0 to 4.0 MPa, yet still more preferably from 2.5 to 4.0 MPa, and even yet still more preferably from 3.0 to 4.0 MPa. From the viewpoint of increasing the trans-isomer content, the hydrogen pressure is preferably from 0.2 to 5 MPa, more preferably from 0.3 to 3 MPa, and still more preferably from 0.3 to 1.5 MPa.

Incidentally, the "hydrogen pressure" as referred to in the present specification means a partial pressure of hydrogen within the pressure-resistant reactor at the time of the hydrogenation reaction.

From the viewpoints of allowing the reaction to gently proceed, thereby decreasing the remaining amount of the reaction intermediate and increasing the content of the trans-isomer occupying in the product, a hydrogenation reaction temperature is preferably from 50 to 300° C., more preferably from 100 to 250° C., and still more preferably from 130 to 200° C. A reaction time is preferably from 1 to 30 hours, more preferably from 2 to 20 hours, and still more preferably from 3 to 10 hours.

The product obtained in the hydrogenation step can be purified by means of filtration, distillation, column chromatography, or the like, as the need arises.

[Perfume Composition]

The perfume composition of the present invention is one containing 1-(2-t-butylcyclohexyloxy)-2-butanol obtained by the above-described production method of the present invention.

From the viewpoints of fragrance and fragrance notes, the content of 1-(2-t-butylcyclohexyloxy)-2-butanol in the perfume composition of the present invention is preferably from 0.01 to 99% by mass, more preferably from 0.1 to 15% by mass, still more preferably from 0.5 to 10% by mass, and yet still more preferably from 1 to 10% by mass.

In addition, the perfume composition of the present invention can contain generally used other perfume component or a formulated perfume having a desired composition.

Examples of other perfume component which can be used include an alcohol other than 1-(2-t-butylcyclohexyloxy)-2-butanol, a hydrocarbon, a phenol, an ester, a carbonate, an aldehyde, a ketone, an acetal, an ether, a carboxylic acid, a lactone, a nitrile, a Schiff base, a natural essential oil, a natural extract, and the like. Of these, an alcohol, an ester, and a lactone are preferable, and an alcohol and an ester are more preferable. These perfume components can be used solely or in combination of two or more kinds thereof.

As for the above-described embodiment, the present invention discloses the following production methods of 1-(2-t-butylcyclohexyloxy)-2-butanol and perfume compositions.

<1> A method of producing 1-(2-t-butylcyclohexyloxy)-2-butanol including a step of hydrogenating 1-(2-t-butylphenyloxy)-2-butanol under a condition at a hydrogen pressure of from 1 MPa or more and not more than 5 MPa in the presence of a palladium catalyst (A) supported on peat-derived active carbon and a metal catalyst (B) containing one or more kinds of members selected from ruthenium, rhodium, platinum, and nickel.

<2> The method of producing 1-(2-t-butylcyclohexyloxy)-2-butanol as set forth above in <1>, wherein the supporting amount of palladium in the palladium catalyst (A) supported on peat-derived active carbon is preferably 0.1% by mass or more, more preferably 0.5% by mass or more, and still more preferably 1% by mass or more, and preferably not more than 15% by mass, more preferably not more than 10% by mass, and still more preferably not more than 5% by mass.

<3> The method of producing 1-(2-t-butylcyclohexyloxy)-2-butanol as set forth above in <1> or <2>, wherein a mass ratio of palladium in the palladium catalyst (A) and one or more kinds of metals selected from ruthenium, rhodium, platinum, and nickel in the metal catalyst (B), [{palladium in the catalyst (A)}/{metal in the catalyst (B)}], is preferably from 80/20 to 99/1, more preferably from 85/15 to 95/5, and still more preferably from 90/10 to 95/5.

<4> The method of producing 1-(2-t-butylcyclohexyloxy)-2-butanol as set forth above in any one of <1> to <3>, wherein the amount of an organic solvent in the hydrogenation step is preferably not more than 50% by mass, more preferably not more than 10% by mass, still more preferably not more than 5% by mass, yet still more preferably not more than 1% by mass, even still more preferably substantially 0% by mass, and even yet still more preferably 0% by mass relative to the 1-(2-t-butylphenyloxy)-2-butanol.

<5> The method of producing 1-(2-t-butylcyclohexyloxy)-2-butanol as set forth above in <4>, wherein the amount of the organic solvent in the hydrogenation step is preferably 0% by mass relative to the 1-(2-t-butylphenyloxy)-2-butanol, and more preferably, the organic solvent is not contained within a reactor in the hydrogenation step.

<6> The method of producing 1-(2-t-butylcyclohexyloxy)-2-butanol as set forth above in any one of <1> to <5>, wherein the carbon content in the peat-derived active carbon which is used for the palladium catalyst (A) is preferably 95% by mass or more, and more preferably 97% by mass or more, and preferably not more than 99.95% by mass, and more preferably not more than 99.9% by mass.

<7> The method of producing 1-(2-t-butylcyclohexyloxy)-2-butanol as set forth above in any one of <1> to <6>, wherein an average pore diameter of the peat-derived active carbon which is used for the palladium catalyst (A) is preferably 8 angstroms or more, and more preferably 30 angstroms or more, and preferably not more than 100 angstroms, and more preferably not more than 60 angstroms.

<8> The method of producing 1-(2-t-butylcyclohexyloxy)-2-butanol as set forth above in any one of <1> to <7>, wherein a pore volume of the peat-derived active carbon (pore volume of pores having a pore diameter of less than 1,000 angstroms) which is used for the palladium catalyst (A) is preferably 0.1 mL/g or more, more preferably 0.2 mL/g or more, and still more preferably 0.3 mL/g or more, and preferably not more than 2.5 mL/g, more preferably not more than 2.0 mL/g, still more preferably not more than 1.5 mL/g, and yet still more preferably not more than 1.0 mL/g.

<9> The method of producing 1-(2-t-butylcyclohexyloxy)-2-butanol as set forth above in any one of <1> to <8>, wherein a pore volume of meso pores of the peat-derived active carbon (pore volume of pores having a pore diameter of from 2 to 50 nm) which is used for the palladium catalyst (A) is preferably 0.21 mL/g or more, more preferably 0.24 mL/g or more, still more preferably 0.27 mL/g or more, and yet still more preferably 0.30 mL/g or more, and preferably not more than 1.0 mL/g, more preferably not more than 0.75 mL/g, and still more preferably not more than 0.4 mL/g.

<10> The method of producing 1-(2-t-butylcyclohexyloxy)-2-butanol as set forth above in any one of <1> to <9>, wherein a specific surface area of the peat-derived active carbon which is used for the palladium catalyst (A) is preferably 100 m$^2$/g or more, and more preferably 150 m$^2$/g or more, and preferably not more than 3,000 m$^2$/g, more preferably not more than 2,000 m$^2$/g, and still more preferably not more than 1,500 m$^2$/g.

<11> The method of producing 1-(2-t-butylcyclohexyloxy)-2-butanol as set forth above in any one of <1> to <10>, wherein the palladium catalyst supported on peat-derived active carbon which is used for the palladium catalyst (A) is preferably one obtained by an impregnation method using a palladium salt.

<12> The method of producing 1-(2-t-butylcyclohexyloxy)-2-butanol as set forth above in any one of <1> to <11>, wherein the palladium salt which is used for the palladium catalyst (A) is preferably one or more kinds of members selected from $Pd(OH)_2$, $PdCl_2$, $Pd(OAc)_2$, $Pd(NH_4)Cl_2$, and $[Pd(NH_3)_4]Cl_2$, more preferably one or more kinds of members selected from $Pd(OH)_2$, $PdCl_2$, and $Pd(OAc)_2$, and still more preferably one or more kinds of members selected from $Pd(OH)_2$ and $PdCl_2$.

<13> The method of producing 1-(2-t-butylcyclohexyloxy)-2-butanol as set forth above in any one of <1> to <12>, wherein the palladium catalyst (A) is one obtained by supporting palladium on peat-derived active carbon; subjecting it to a reducing treatment at a temperature of preferably 20° C. or higher and not higher than 300° C., and more preferably 80° C. or higher and not higher than 280° C.; carrying out solid-liquid separation; and washing the obtained solid with water, followed by drying.

<14> The method of producing 1-(2-t-butylcyclohexyloxy)-2-butanol as set forth above in any one of <1> to <13>, wherein the pH of a mixture obtained by mixing the palladium catalyst (A) with pure water in an amount of 10 times by mass is preferably 7.0 or more and not more than 12.0, more preferably 7.0 or more, still more preferably 7.5 or more, yet still more preferably 7.8 or more, and even yet still more preferably 7.9 or more, and more preferably not more than 10.0, still more preferably not more than 9.5, yet still more preferably not more than 9.0, even still more preferably not more than 8.9, and even yet still more preferably not more than 8.8.

<15> The method of producing 1-(2-t-butylcyclohexyloxy)-2-butanol as set forth above in any one of <1> to <14>, wherein the metal catalyst (B) is preferably a supported catalyst supported on a carrier.

<16> The method of producing 1-(2-t-butylcyclohexyloxy)-2-butanol as set forth above in any one of <1> to <15>, wherein the metal component of the metal catalyst (B) is preferably one or more kinds of members selected from ruthenium, rhodium, and platinum, more preferably one or more kinds of members selected from ruthenium and rhodium, and still more preferably ruthenium.

<17> The method of producing 1-(2-t-butylcyclohexyloxy)-2-butanol as set forth above in any one of <1> to <16>, wherein the carrier of the metal catalyst (B) is preferably an inorganic carrier, more preferably one or more kinds of carriers selected from active carbon, alumina, silica, silica magnesia, and zeolite, and still more preferably active carbon.

<18> The method of producing 1-(2-t-butylcyclohexyloxy)-2-butanol as set forth above in any one of <1> to <17>, wherein the supporting amount of the metal component of the metal catalyst (B) is preferably 0.05% by mass or more and not more than 20% by mass, more preferably 0.1% by mass or more, and still more preferably 0.5% by mass or more, and more preferably not more than 15% by mass, and still more preferably not more than 10% by mass of the whole of the metal catalyst (B).

<19> The method of producing 1-(2-t-butylcyclohexyloxy)-2-butanol as set forth above in any one of <1> to <18>, wherein the pH of the metal catalyst (B) is preferably 6.0 or more and not more than 12.0, more preferably 7.0 or more, and still more preferably 7.2 or more, and more preferably not more than 9.0, and still more preferably not more than 8.0.

<20> The method of producing 1-(2-t-butylcyclohexyloxy)-2-butanol as set forth above in any one of <1> to <19>, wherein a total use amount of the palladium catalyst (A) and the metal catalyst (B) is preferably 0.01% by mass or more and not more than 10% by mass, and more preferably 0.05% by mass or more and not more than 5% by mass relative to 1-(2-t-butylphenyloxy)-2-butanol as the raw material.

<21> The method of producing 1-(2-t-butylcyclohexyloxy)-2-butanol as set forth above in any one of <1> to <20>, wherein the palladium catalyst (A) contains one or more kinds of metals selected from iron, magnesium, manganese, calcium, and titanium in a total content of preferably 0.10% or more, more preferably 0.15% or more, still more preferably 0.20% or more, and yet still more preferably 0.24% or more, and preferably not more than 1.0%, more preferably not more than 0.80%, still more preferably not more than 0.50%, and yet still more preferably not more than 0.40% in the palladium catalyst (A).

<22> The method of producing 1-(2-t-butylcyclohexyloxy)-2-butanol as set forth above in any one of <1> to <21>, wherein the palladium catalyst (A) contains nitrogen in an amount of preferably 0.07% or more, more preferably 0.08% or more, still more preferably 0.09% or more, and yet still more preferably 0.10% or more, and preferably not more than 1.0%, more preferably not more than 0.50%, still more preferably not more than 0.20%, and yet still more preferably not more than 0.15% in the palladium catalyst (A).

<23> The method of producing 1-(2-t-butylcyclohexyloxy)-2-butanol as set forth above in any one of <1> to <22>, wherein the palladium catalyst (A) contains sulfur in an amount of preferably 0.08% or more, more preferably 0.09% or more, still more preferably 0.10% or more, and yet still more preferably 0.11% or more, and preferably not more than 1.0%, more preferably not more than 0.50%, still more preferably not more than 0.20%, and yet still more preferably not more than 0.15% in the palladium catalyst (A).

<24> The method of producing 1-(2-t-butylcyclohexyloxy)-2-butanol as set forth above in any one of <1> to <23>, wherein the organic solvent which is used for the hydrogenation reaction is preferably one or more kinds of members selected from an alcohol and a hydrocarbon, more preferably an alcohol, still more preferably one or more kinds of members selected from methanol, ethanol, and isopropanol, and yet still more preferably isopropanol.

<25> The method of producing 1-(2-t-butylcyclohexyloxy)-2-butanol as set forth above in any one of <1> to <24>, wherein the hydrogen pressure is preferably 1.5 MPa or more, more preferably 2.0 MPa or more, still more preferably 2.5 MPa or more, and yet still more preferably 3.0 MPa or more, and preferably not more than 4 MPa.

<26> The method of producing 1-(2-t-butylcyclohexyloxy)-2-butanol as set forth above in any one of <1> to <25>, wherein a hydrogenation reaction temperature is preferably 50° C. or higher, more preferably 100° C. or higher, and still more preferably 130° C. or higher, and preferably not higher than 300° C., more preferably not higher than 250° C., and still more preferably not higher than 200° C.

<27> A perfume composition containing 1-(2-t-butylcyclohexyloxy)-2-butanol obtained by the method as set forth above in any one of <1> to <26>.

<28> The perfume composition as set forth above in <27>, wherein the content of the 1-(2-t-butylcyclohexyloxy)-2-butanol in the perfume composition is preferably 0.01% by mass or more, more preferably 0.1% by mass or more, still more preferably 0.5% by mass or more, and yet still more preferably 1% by mass or more, and preferably not more than 99% by mass, more preferably not more than 15% by mass, and still more preferably not more than 10% by mass.

<29> The perfume composition as set forth above in <27> or <28>, wherein the perfume composition preferably contains one or more members selected from an alcohol other than 1-(2-t-butylcyclohexyloxy)-2-butanol, a hydrocarbon, a phenol, an ester, a carbonate, an aldehyde, a ketone, an acetal, an ether, a carboxylic acid, a lactone, a nitrile, a Schiff base, a natural essential oil, and a natural extract.

<30> Use of 1-(2-t-butylcyclohexyloxy)-2-butanol obtained by the production method as set forth above in any one of <1> to <26> as a perfume.

EXAMPLES

In the following Examples and Comparative Examples, the term "%" is "% by mass" unless otherwise indicated. In addition, the mass of the catalyst is a mass in a dry state.

Production of 1-(2-t-butylcyclohexyloxy)-2-butanol

Example 1

In a 500-mL autoclave, 250 g of 1-(2-t-butylphenyloxy)-2-butanol, 4.75 g of a peat-derived active carbon-supported palladium catalyst (manufactured by N.E. Chemcat Corporation, a trade name: U Type, a 50% hydrated product, supporting amount of palladium: 2%, use of gas-activated active carbon, pH: 7.9, pore volume (pore volume of pores having a pore diameter of less than 1,000 angstroms—hereinafter the same in the following Examples and Comparative Examples): 0.36 mL/g, specific surface area: 180 m$^2$/g, pore volume of meso pores (pore volume of pores having a pore diameter of from 2 to 50 nm—hereinafter the same in the following Examples and Comparative Examples): 0.28 mL/g, metal content: 0.25%, nitrogen content: 0.10%, sulfur content: 0.13%), and 0.25 g of an active carbon-supported ruthenium catalyst (manufactured by N.E. Chemcat Corporation, a 50% hydrated product, supporting amount of ruthenium: 5%, use of gas-activated active carbon, pH: 7.2) were added and allowed to react at a hydrogen pressure of 2.0 MPa and 190° C. for 6 hours.

After termination of the reaction, the catalysts were filtered, and distillation was carried out to obtain 1-(2-t-butylcyclohexyloxy)-2-butanol in a yield of 73%. As a result of analyzing the product by means of gas chromatography, the amount of a cyclic ketal (remaining amount of a reaction intermediate) relative to 1-(2-t-butylcyclohexyloxy)-2-butanol was 0%, and a ratio (mass ratio) of cis-isomer/trans-isomer of 1-(2-t-butylcyclohexyloxy)-2-butanol was found to be 55/45. The analysis was carried out in the same manner in the following Examples and Comparative Examples. Results are shown in Table 1.

Example 2

1-(2-t-Butylcyclohexyloxy)-2-butanol was obtained by carrying out the reaction in the same manner as that in Example 1, except that in Example 1, the hydrogen pressure was changed from 2.0 MPa to 4.0 MPa. Results are shown in Table 1.

Comparative Example 1

1-(2-t-Butylcyclohexyloxy)-2-butanol was obtained by carrying out the reaction in the same manner as that in Example 1, except that in Example 1, the hydrogen pressure was changed from 2.0 MPa to 0.5 MPa. Results are shown in Table 1.

Comparative Example 2

1-(2-t-Butylcyclohexyloxy)-2-butanol was obtained by carrying out the reaction in the same manner as that in Example 1, except that in Example 1, the hydrogen pressure was changed from 2.0 MPa to 7.0 MPa. Results are shown in Table 1.

Example 3

1-(2-t-Butylcyclohexyloxy)-2-butanol was obtained by carrying out the reaction in the same manner as that in Example 1, except that in Example 1, the peat-derived active carbon-supported palladium catalyst was changed from the U Type to S Type (manufactured by N.E. Chemcat Corporation, a 50% hydrated product, supporting amount of palladium: 2%, use of gas-activated active carbon, pH: 7.9, pore volume: 0.37 mL/g, specific surface area: 175 $m^2$/g, pore volume of meso pores: 0.32 mL/g, metal content: 0.29%, nitrogen content: 0.13%, sulfur content: 0.12%). Results are shown in Table 1.

Comparative Example 3

1-(2-t-Butylcyclohexyloxy)-2-butanol was obtained by carrying out the reaction in the same manner as that in Example 1, except that in Example 1, the peat-derived active carbon-supported palladium catalyst was changed to a charcoal-derived active carbon-supported palladium catalyst (manufactured by N.E. Chemcat Corporation, a trade name: D Type, a 50% hydrated product, supporting amount of palladium: 2%, pH: 8.2, pore volume: 0.25 mL/g, specific surface area: 146 $m^2$/g, pore volume of meso pores: 0.20 mL/g, metal content: 0.07%, nitrogen content: 0.06%, sulfur content: 0.07%). Results are shown in Table 1.

Example 4

1-(2-t-Butylcyclohexyloxy)-2-butanol was obtained by carrying out the reaction in the same manner as that in Example 1, except that in Example 1, the hydrogen pressure was changed from 2.0 MPa to 5.0 MPa; the amount of the 1-(2-t-butylphenyloxy)-2-butanol was changed to 50 g; the amount of the active carbon-supported palladium catalyst was changed to 0.95 g; the amount of the active carbon-supported ruthenium catalyst was changed to 0.05 g; and 150 g of isopropanol was further added. Results are shown in Table 1.

Example 5

1-(2-t-Butylcyclohexyloxy)-2-butanol was obtained by carrying out the reaction in the same manner as that in Example 1, except that in Example 1, the amount of the peat-derived active carbon-supported palladium catalyst (manufactured by N.E. Chemcat Corporation, a trade name: U Type, a 50% hydrated product, supporting amount of palladium: 2%, use of gas-activated active carbon, pH: 7.9, pore volume: 0.36 mL/g, specific surface area: 180 $m^2$/g, pore volume of meso pores: 0.28 mL/g, metal content: 0.25%, nitrogen content: 0.10%, sulfur content: 0.13%) was changed to 0.98 g; the amount of the active carbon-supported ruthenium catalyst (manufactured by N.E. Chemcat Corporation, a 50% hydrated product, supporting amount of ruthenium: 5%, use of gas-activated active carbon, pH: 7.2) was changed to 0.02 g; the hydrogen pressure was changed from 2.0 MPa to 5.0 MPa; the amount of the 1-(2-t-butylphenyloxy)-2-butanol was changed to 50 g; and 150 g of isopropanol was further added. Results are shown in Table 1.

Comparative Example 4

1-(2-t-Butylcyclohexyloxy)-2-butanol was obtained by carrying out the reaction in the same manner as that in Example 1, except that in Example 1, the amount of the peat-derived active carbon-supported palladium catalyst (manufactured by N.E. Chemcat Corporation, a trade name: U Type, a 50% hydrated product, supporting amount of palladium: 2%, use of gas-activated active carbon, pH: 7.9, pore volume: 0.36 mL/g, specific surface area: 180 $m^2$/g, pore volume of meso pores: 0.28 mL/g, metal content: 0.25%, nitrogen content: 0.10%, sulfur content: 0.13%) was changed to 0.98 g; the amount of the active carbon-supported ruthenium catalyst (manufactured by N.E. Chemcat Corporation, a 50% hydrated product, supporting amount of ruthenium: 5%, use of gas-activated active carbon, pH: 7.2) was changed to 0.02 g; the hydrogen pressure was changed from 2.0 MPa to 7.0 MPa; the amount of the 1-(2-t-butylphenyloxy)-2-butanol was changed to 50 g; and 150 g of isopropanol was further added. Results are shown in Table 1.

Comparative Example 5

1-(2-t-Butylcyclohexyloxy)-2-butanol was obtained by carrying out the reaction in the same manner as that in Example 1, except that in Example 1, the peat-derived active carbon-supported palladium catalyst was changed to 0.98 g of a charcoal-derived active carbon-supported palladium catalyst (manufactured by N.E. Chemcat Corporation, a trade name: C Type, a 50% hydrated product, supporting amount of palladium: 2%, pH: 8.0, pore volume: 0.23 mL/g, specific surface area: 137 $m^2$/g, pore volume of meso pores: 0.14 mL/g, metal content: 0.09%, nitrogen content: 0.05%, sulfur content: 0.06%); the amount of the active carbon-supported ruthenium catalyst (manufactured by N.E. Chemcat Corporation, a 50% hydrated product, supporting amount of ruthenium: 5%, use of gas-activated active carbon, pH: 7.2) was changed to 0.02 g; the hydrogen pressure was changed from 2.0 MPa to 7.0 MPa; the amount of the 1-(2-t-butylphenyloxy)-2-butanol was changed to 50 g; and 150 g of isopropanol was further added. Results are shown in Table 1.

Comparative Example 6

1-(2-t-Butylcyclohexyloxy)-2-butanol was obtained by carrying out the reaction in the same manner as that in Example 1, except that in Example 1, the amount of the peat-derived active carbon-supported palladium catalyst (manufactured by N.E. Chemcat Corporation, a trade name: U Type, a 50% hydrated product, supporting amount of palladium: 2%, use of gas-activated active carbon, pH: 7.9, pore volume: 0.36 mL/g, specific surface area: 180 $m^2$/g, pore volume of meso pores: 0.28 mL/g, metal content: 0.25%, nitrogen content: 0.10%, sulfur content: 0.13%) was changed to 0.98 g; the amount of the active carbon-supported ruthenium catalyst (manufactured by N.E. Chemcat Corporation, a 50% hydrated product, supporting amount of ruthenium: 5%, use of gas-activated active carbon, pH: 7.2) was changed to 0.02 g; the hydrogen pressure was changed from 2.0 MPa to 7.0 MPa; the amount of the 1-(2-t-butylphenyloxy)-2-butanol was changed to 50 g; and 2.5 g of isopropanol was further added. Results are shown in Table 1.

Example 6

1-(2-t-Butylcyclohexyloxy)-2-butanol was obtained by carrying out the reaction in the same manner as that in Example 5, except that in Example 5, the amount of the isopropanol was changed from 150 g to 2.5 g. Results are shown in Table 1.

Test Example

With respect to the 1-(2-t-butylcyclohexyloxy)-2-butanol obtained in each of Examples 1 to 6 and Comparative Examples 1 to 6, the fragrance notes were evaluated by the following method. Results are shown in Table 1.

<Evaluation Method of Fragrance Notes>

The fragrance notes were evaluated by plural expert panelists. The fragrance was enumerated in the order from one which was felt stronger. With respect to the evaluation sample having a characteristic in the fragrance notes, its decision was also added. The overall evaluation was ranked according to the following criteria.

A: The evaluation sample is extremely interesting, and its value as a perfume material is high.

B: The evaluation sample has a sufficient value as a perfume material.

C: The evaluation sample has a substantially sufficient value as a perfume material.

D: The evaluation sample has a slightly low value as a perfume material.

TABLE 1

| | | Example 1 | Example 2 | Comparative Example 1 | Comparative Example 2 | Example 3 | Comparative Example 3 |
|---|---|---|---|---|---|---|---|
| Reaction condition | | | | | | | |
| Organic solvent | Type *1 | None | None | None | None | None | None |
| | [%] *2 | 0 | 0 | 0 | 0 | 0 | 0 |
| Catalyst (A) | Metal | Palladium | Palladium | Palladium | Palladium | Palladium | Palladium |
| | Carrier | Peat-derived active carbon (U) | Peat-derived active carbon (U) | Peat-derived active carbon (U) | Peat-derived active carbon (U) | Peat-derived active carbon (S) | Charcoal-derived active carbon |
| Catalyst (B) | Metal | Ruthenium | Ruthenium | Ruthenium | Ruthenium | Ruthenium | Ruthenium |
| | Carrier | Active carbon | Active carbon | Active carbon | Active carbon | Active carbon | Active carbon |
| [Pd—(A)/M-(B)] *3 | | 88.4/11.6 | 88.4/11.6 | 88.4/11.6 | 88.4/11.6 | 88.4/11.6 | 88.4/11.6 |
| Hydrogen pressure | [MPa] | 2.0 | 4.0 | 0.5 | 7.0 | 2.0 | 2.0 |
| Reaction temperature | [° C.] | 190 | 190 | 190 | 190 | 190 | 190 |
| Results | | | | | | | |
| Yield | [%] | 72 | 83 | 38 | 71 | 75 | 61 |
| Remaining amount of reaction intermediate | [%] | 0 | 0 | 54 | 3 | 0 | 18 |
| Evaluation | | | | | | | |
| Fragrance notes | | Strongly amber-like Woody Slightly camphor-like | Strongly amber-like Woody Slightly camphor-like | Strongly amber-like Woody Slightly camphor-like | Strongly amber-like Woody Slightly camphor-like | Strongly amber-like Woody Slightly camphor-like | Amber-like Woody Slightly camphor-like |
| Ratio of trans-isomer | [%] *4 | 45 | 44 | 46 | 43 | 45 | 37 |
| Decision | | Sweet and voluminous | Sweet and voluminous | Sweet and voluminous | Sweet and voluminous | Sweet and voluminous | — |
| Overall evaluation | | A | A | A | A | A | C |

| | | Example 4 | Example 5 | Comparative Example 4 | Comparative Example 5 | Comparative Example 6 | Example 6 |
|---|---|---|---|---|---|---|---|
| Reaction condition | | | | | | | |
| Organic solvent | Type *1 | isoPrOH | isoPrOH | isoPrOH | isoPrOH | isoPrOH | isoPrOH |
| | [%] *2 | 300 | 300 | 300 | 300 | 5 | 5 |
| Catalyst (A) | Metal | Palladium | Palladium | Palladium | Palladium | Palladium | Palladium |
| | Carrier | Peat-derived active carbon (U) | Peat-derived active carbon (U) | Peat-derived active carbon (U) | Charcoal-derived active carbon | Peat-derived active carbon (U) | Peat-derived active carbon (U) |
| Catalyst (B) | Metal | Ruthenium | Ruthenium | Ruthenium | Ruthenium | Ruthenium | Ruthenium |
| | Carrier | Active carbon | Active carbon | Active carbon | Active carbon | Active carbon | Active carbon |
| [Pd—(A)/M-(B)] *3 | | 88.4/11.6 | 95.1/4.9 | 95.1/4.9 | 95.1/4.9 | 95.1/4.9 | 95.1/4.9 |
| Hydrogen pressure | [MPa] | 5.0 | 5.0 | 7.0 | 7.0 | 7.0 | 5.0 |
| Reaction temperature | [° C.] | 190 | 190 | 190 | 190 | 190 | 190 |
| Results | | | | | | | |
| Yield | [%] | 85 | 82 | 84 | 81 | 79 | 81 |
| Remaining amount of reaction intermediate | [%] | 0 | 0 | 5 | 10 | 5 | 0 |
| Evaluation | | | | | | | |
| Fragrance notes | | Strongly amber-like Woody Slightly camphor-like | Strongly amber-like Woody Slightly camphor-like | Amber-like Woody Slightly camphor-like | Amber-like Woody Slightly camphor-like | Amber-like Woody Slightly camphor-like | Strongly amber-like Woody Slightly camphor-like |

TABLE 1-continued

| | | | | | | |
|---|---|---|---|---|---|---|
| Ratio of trans-isomer [%] *4 | 39 | 39 | 33 | 37 | 44 | 43 |
| Decision | Sweet | Sweet | — | — | Sweet and voluminous | Sweet and voluminous |
| Overall evaluation | B | B | C | C | A | A |

*1 isoPrOH: Isopropyl alcohol
*2 Amount of the organic solvent relative to 1-(2-t-butylphenyloxy)-2-butanol
*3 Mass ratio of {palladium in the palladium catalyst (A)}/{metal in the metal catalyst (B)}
*4 Proportion of the trans-isomer of 1-(2-t-butylcyclohexyloxy)-2-butanol Formulating Example To 920 parts by mass of a floral oriental-note formulated perfume having the following composition, 80 parts by mass of the perfume composition of the present invention obtained in Example 1 was added. As a result, the powdery sweetness was strengthened.

<Composition of floral oriental-note formulated perfume>

| | |
|---|---|
| Bergamot oil: | 80 parts by mass |
| Dihydromyrcenol: | 25 parts by mass |
| Allyl-2-pentyloxyglycolate: | 5 parts by mass |
| Methyl phenyl carbinyl acetate: | 10 parts by mass |
| Ylang-ylang base: | 50 parts by mass |
| Rose base: | 50 parts by mass |
| Jasmine base: | 100 parts by mass |
| Methyl dihydrojasmonate: | 130 parts by mass |
| Methyl ionone gamma: | 150 parts by mass |
| SANDALMYSORE CORE *1: | 50 parts by mass |
| TONALIDE *2: | 100 parts by mass |
| Benzyl salicylate: | 50 parts by mass |
| Coumarin: | 50 parts by mass |
| Vanillin: | 20 parts by mass |
| Amber base: | 50 parts by mass |
| | 920 parts by mass |

(Note)
*1: 2-Methyl-4-(2,3,3-trimethyl-3-cyclopentyn-1-yl)-2-buten-1-ol, manufactured by Kao Corporation
*2: 7-Acetyl-1,1,3,4,4,6-hexamethyltetrahydronaphthalene, manufactured by PFW Aroma Chemicals B.V.

INDUSTRIAL APPLICABILITY

According to the production method of the present invention, 1-(2-t-butylcyclohexyloxy)-2-butanol having a woody or amber-like fragrance as a perfume material and excellent fragrance notes can be obtained in a high purity because of a small remaining amount of a reaction intermediate and in a high yield. The produced 1-(2-t-butylcyclohexyloxy)-2-butanol can be used as a perfume material for an aromatizing component of, for example, soaps, shampoos, conditioners, detergents, toiletries, spray products, aromatics, perfumeries, bath salts, etc.

The invention claimed is:

1. A method of producing 1-(2-t-butylcyclohexyloxy)-2-butanol, comprising:
hydrogenating 1-(2-t-butylphenyloxy)-2-butanol under a condition at a hydrogen pressure of from 1 to 5 MPa in the presence of a palladium catalyst (A) supported on peat-derived active carbon and a metal catalyst (B) comprising at least one member selected from the group consisting of ruthenium, rhodium, platinum, and nickel.

2. The method of producing 1-(2-t-butylcyclohexyloxy)-2-butanol according to claim 1, wherein the supporting amount of palladium in the palladium catalyst (A) supported on peat-derived active carbon is from 0.1 to 15% by mass.

3. The method of producing 1-(2-t-butylcyclohexyloxy)-2-butanol according to claim 1, wherein a mass ratio of palladium in the palladium catalyst (A) and the at least one metal selected from the group consisting of ruthenium, rhodium, platinum, and nickel in the metal catalyst (B), [{palladium in the catalyst (A)}/{metal in the catalyst (B)}], is from 80/20 to 99/1.

4. The method of producing 1-(2-t-butylcyclohexyloxy)-2-butanol according to claim 1, wherein an amount of an organic solvent present during said hydrogenating is not more than 10% by mass relative to the 1-(2-t-butylphenyloxy)-2-butanol.

5. The method of producing 1-(2-t-butylcyclohexyloxy)-2-butanol according to claim 4, wherein the amount of the organic solvent in said hydrogenating is 0% by mass relative to the 1-(2-t-butylphenyloxy)-2-butanol.

6. The method of producing 1-(2-t-butylcyclohexyloxy)-2-butanol according to claim 1, wherein the palladium catalyst supported on peat-derived active carbon of palladium catalyst (A) is one obtained by an impregnation method with a palladium salt.

7. The method of producing 1-(2-t-butylcyclohexyloxy)-2-butanol according to claim 6, wherein the palladium salt is at least one member selected from the group consisting of $Pd(OH)_2$, $PdCl_2$, $Pd(OAc)_2$, $Pd(NH_4)Cl_2$, and $[Pd(NH_3)_4]Cl_2$.

8. The method of producing 1-(2-t-butylcyclohexyloxy)-2-butanol according to claim 1, wherein the pH of a mixture obtained by mixing the palladium catalyst (A) with pure water in an amount of 10 times by mass is from 7.0 to 12.0.

9. The method of producing 1-(2-t-butylcyclohexyloxy)-2-butanol according to claim 1, wherein a total amount of the palladium catalyst (A) and the metal catalyst (B) is from 0.01 to 10% by mass relative to 1-(2-t-butylphenyloxy)-2-butanol as the raw material.

10. The method of producing 1-(2-t-butylcyclohexyloxy)-2-butanol according to claim 1, wherein the palladium catalyst (A) comprises a metal selected at least one of iron, magnesium, manganese, calcium, and titanium in an amount of 0.10% or more and not more than 1.0% in the palladium catalyst (A).

11. The method of producing 1-(2-t-butylcyclohexyloxy)-2-butanol according to claim 1, wherein the palladium catalyst (A) comprises nitrogen in an amount of 0.07% or more and not more than 1.0% in the palladium catalyst (A).

12. The method of producing 1-(2-t-butylcyclohexyloxy)-2-butanol according to claim 1, wherein the palladium catalyst (A) comprises sulfur in an amount of 0.08% or more and not more than 1.0% in the palladium catalyst (A).

13. The method of producing 1-(2-t-butylcyclohexyloxy)-2-butanol according to claim 4, wherein the organic solvent is at least one member selected from an alcohol and a hydrocarbon.

14. The method of producing 1-(2-t-butylcyclohexyloxy)-2-butanol according to claim 1, wherein a hydrogenation reaction temperature is from 50 to 300° C.

15. The method of producing 1-(2-t-butylcyclohexyloxy)-2-butanol according to claim 1, wherein the palladium catalyst (A) is one obtained by supporting palladium on peat-derived active carbon; subjecting it to a reducing treatment at a temperature of 20° C. or higher and not higher than 300° C.; carrying out solid-liquid separation; and washing the obtained solid with water, followed by drying.

16. The method of producing 1-(2-t-butylcyclohexyloxy)-2-butanol according to claim 1, wherein the carbon content in the peat-derived active carbon is 95% by mass or more and not more than 99.95% by mass.

17. The method of producing 1-(2-t-butylcyclohexyloxy)-2-butanol according to claim 1, wherein an average pore diameter of the peat-derived active carbon is 8 angstroms or more and not more than 100 angstroms.

18. The method of producing 1-(2-t-butylcyclohexyloxy)-2-butanol according to claim 1, wherein a pore volume of the peat-derived active carbon (pore volume of pores having a pore diameter of less than 1,000 angstroms) is 0.1 mL/g or more and not more than 2.0 mL/g.

19. The method of producing 1-(2-t-butylcyclohexyloxy)-2-butanol according to claim 1, wherein the metal catalyst (B) is a supported catalyst supported on a carrier.

20. The method of producing 1-(2-t-butylcyclohexyloxy)-2-butanol according to claim 1, wherein a total amount of the palladium catalyst (A) and the metal catalyst (B) is 0.05% by mass or more and not more than 5% by mass relative to 1-(2-t-butylphenyloxy)-2-butanol as the raw material.

* * * * *